United States Patent [19]

Cardin

[11] Patent Number: 4,832,849
[45] Date of Patent: May 23, 1989

[54] **EXTRACTION AND PURIFICATION OF AN ANTICOAGULANT PRINCIPLE FROM THE SOUTH AMERICAN LEECH, *HAEMENTERIA GHILIANII***

[75] Inventor: Alan D. Cardin, Cincinnati, Ohio

[73] Assignee: Merrell Dow Pharmaceuticals Inc., Cincinnati, Ohio

[21] Appl. No.: 207,415

[22] Filed: Jun. 16, 1988

[51] Int. Cl.$^4$ .............................................. B01D 15/08
[52] U.S. Cl. .................................... 210/635; 210/656; 424/94.63; 424/94.64; 424/95; 435/212; 435/219; 435/226; 435/815; 514/21; 514/822; 530/324; 530/344; 530/350; 530/413; 530/416; 530/417; 530/855
[58] Field of Search .............................. 210/635, 656; 424/94.63, 94.64, 95; 435/212, 219, 226, 815; 514/21, 822; 530/344, 413, 416, 417, 855, 324, 350

[56] References Cited

U.S. PATENT DOCUMENTS

| | | | |
|---|---|---|---|
| 3,300,383 | 1/1967 | Markwardt | 514/21 |
| 3,432,596 | 11/1969 | Markwardt | 424/95 |
| 4,390,630 | 1/1983 | Sawyer | 424/94.64 |
| 4,588,587 | 5/1986 | Gasic | 424/95 |

OTHER PUBLICATIONS

Derwent Abstract, European Patent Application No. 193,330, Feb. 1985.
Derwent Abstract, West German Patent Appln. No. 3,445,532, Dec. 1984.
Derwent Abstract, U.S. Pat. No. 4,588,587, Mar. 1983.
Derwent Abstract, U.S. Pat. No. 4,390,630, Jun. 1983.
Derwent Abstract, West German Patent Appln. No. 2,808,396, Apr. 1984.
French Patent Application No. 3792M, Jan. 1966.
East German Patent Application No. 39519, Jun. 1965.
West German Patent Application No. 1,176,316, Aug. 1964.
A. Z. Budzynski et al., "Composition of Salivary Gland Extracts from the Leech *Haementeria ghiliani*", *Proceedings of Society for Experimental Biology and Medicine 168*, 259–265, Jun. 1981.
G. J. Gasic, et al., "Isolation of a Protein from Salivary Glands SGE) of the Leech *Haementeria officinalis* with Potent Antimetastatic and Anticoagulant Activity", *Proceedings of AACR vol. 27*, (Mar. 1986).
European Patent Appln. Publication No. 0 263 608, Apr. 1988.
E. Nutt, et al., "The Amino Acid Sequence of Antistasin", *Journal of Biological Chemistry, vol. 263*, No. 21, 10162–10167, Jul. 1988.

*Primary Examiner*—Ernest G. Therkorn
*Attorney, Agent, or Firm*—Stephen L. Nesbitt

[57] ABSTRACT

Applicant has isolated a Factor $X_a$ inhibiting substance from the salivary gland extract of the leech *H.ghilianii*. The extract is subjected to separation using both DEAE-cellulose and heparin-agarose chromatography resins eluting with an increasing salt gradient. The extract is subjected to affinity chromatography using Factor $X_a$ bound to an Affi-Gel-15 resin eluting with HEPES containing benzamidine. Reverse phase chromatography yields several purified peptides or proteins having Factor $X_a$ inhibiting activity. The properties and clinical compositions of these $FX_a$ inhibitors are described.

3 Claims, 7 Drawing Sheets

EXTRACTION AND PURIFICATION OF AN ANTICOAGULANT PRINCIPLE FROM THE SOUTH AMERICAN LEECH, *HAEMENTERIA GHILIANII*

FIELD OF INVENTION

This invention relates to a proteinaceous substance having Factor $X_a$ inhibition activity and the process of its isolation from the saliva or salivary glands of the leech *Haementeria ghilianii* using chromatographic separation techniques.

BACKGROUND OF INVENTION

Anticoagulants are useful therapeutic agents in the pharmacological treatment of, for example, acute deep venous thrombosis, pulmonary embolism, acute arterial embolization of the extremities, myocardial infarction, and disseminated intravascular coagulation. Prophylactic administration of anticoagulants is believed to prevent a recurrance of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

Blood coagulation depends on many enzymes and cofactors for its success and proceeds by two separate pathways, the intrinsic and extrinsic pathways. In the intrinsic or cascade pathway, all factors are present in circulating blood, but coagulation by this mechanism once initiated takes several minutes to accomplish. In the extrinsic pathway certain lipoproteins, i.e., Factor III, not normally present in circulating blood, are released by damaged cells, and coagulation begins within seconds. These pathways converge at a point in the coagulation process where Factor $X_a$, together with Factor V and calcium ion, form the prothrombinase complex to catalyze the conversion of prothrombin to thrombin. Thus, Factor $X_a$ is of vital importance to both coagulation pathways and its inhibition would reduce blood coagulation regardless of cause. While several inhibitors of Factor $X_a$ are known, such inhibitors are either of the chloroketone class which are quite toxic or are non-specific inhibitors of serine proteases. Thus, a specific and non-toxic inhibitor of Factor Xa would have important therapeutic value.

Leeches have been used medicinally since antiquity. The medicinal use of leeches in the early 19th century, caused the near extinction of the species *Hirudo medicinalis* and caused Russia to impose quotas of its export. More recently, leech secretions have been more scientifically studied and have been found to contain a variety of biological products having a wide spectrum of biochemical and pharmacological activities such as anticoagulant, antimetastatic, anaesthetic, antibiotic, and vasodilator. For example, Hirudin isolated from the salivary gland of the leech *Hirudo medicinalis* is the most specific and potent thrombin inhibitor known. Further, Hementin which is isolated from the salivary gland of the leech *Haementeria ghilianii* is a fibrin(ogen)olytic enzyme of reported high molecular weight. It is reportedly the anticoagulant principle of this leech. This enzyme degrades fibrinogen and fibrin rather than activating the host fibrinolytic system or inhibiting the coagulation system.

Applicant has identified and isolated from the saliva and extracts of salivary gland tissues of the leech *Haementeria ghilianii*, a proteinaceous substance which is a specific inhibitor of Factor $X_a$ and which is a useful inhibitor of blood coagulation.

SUMMARY OF THE INVENTION

The proteinaceous substance having Factor $X_a$ inhibiting activity originating from the salivary gland of the leech *Haementeria ghilianii* and isolated therefrom is a useful anticoagulant agent. The substance is isolated by subjecting the leech saliva or salivary gland extract of the leech *Haementeria ghilianii* to chromatographic separation using an anionic exchange resin and eluting with an increasing salt gradient. Those fractions having high Factor $X_a$ inhibiting activity and anticoagulant activity are then subjected to reverse phase high pressure liquid chromatography (HPLC) to purify further the substance having Factor $X_a$ inhibiting activity.

DETAILED DESCRIPTION OF THE INVENTION

The term saliva as used herein includes not only saliva (or salivary secretions) but homogenized tissue from the whole leech as well as any part of the leech, particularly the salivary glands. The term saliva includes, as well, any isolate of the saliva so long as, of course, the isolate or tissue homogenate contains the proteinacous substance of this invention having Factor $X_a$ inhibiting activity. A proteinaceous substance similar in activity to this invention may also be found in the saliva of other species of Haementeria such as *H. officinalis*.

The proteinacous substance of this invention having Factor $X_a$ inhibiting activity is believed to be comprised of several sequence related proteins with at least two of these proteins being primarily responsible for the Factor $X_a$ inhibiting activity. For the purposes of this invention, all the proteins/peptides having substantial Factor $X_a$ inhibiting activity, that is, having an $IC_{50}$ of at least 1000 $\eta M$, individually and in combinations, such as the combination isolated by the process of this invention from the saliva of the leech *Haementeria ghilianii*, are intended. Applicant specifically intends that the proteinaceous substance of this invention include such substance however derived whether through sequential and block synthesis or through gene cloning and expression.

While the complete amino acid sequence of these peptides is not yet known, certain properties have been ascertained. The peptides comprising the proteinaceous substance of this invention have a molecular weight of about 18 kdal and are not highly glycosylated. While some sugar groups may be present, applicant has found that apparent molecular weight does not vary significantly with polyacrylamide gel concentration in the SDS PAGE determination, suggesting lack of significant glycosyl groups on the peptides. Applicant has also found that each peptide has about 6 alanine residues, 5 methionine residues, 12–14 lysine residues, 18–21 arginine residues, and 16–17 proline residues and a low abundancy of aromatic residues, such as, 4 phenylalanine and 6 tryosyl residues, when amino acid analysis is performed. More precise composition information, such as the number of cysteine/cystine and tryptophan residues, awaits availability of larger quantities of peptide and sequence analysis.

The following common abbrevations of the amino acids are used throughout this specification:

Ala (or A)—alanine
Arg (or R)—arginine
Asx—asparagine and/or aspartic acid
Gly (or G)—glycine
Glx—glutamine acid and/or glutamine
His (or H)—histidine
Leu (or L)—leucine
Lys (or K)—lysine
Met (or M)—methionine
Phe (or F)—phenylalanine
Pro (or P)—proline
Ser (or S)—serine
Thr (or T)—threonine
Tyr (or Y)—tyrosine
Val (or V)—valine The proteinaceous substance of this invention having Factor $X_a$ inhibition activity can, like many proteins/peptides, form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine; N,N'-dibenzylethylenediamine, dihydroabietylamine, N-(lower)alkylpiperidine, and any other suitable amine.

The anticoagulant dose of the proteinaceous substance of this invention having Factor $X_a$ inhibition activity is from 0.2 mg/kg to 250 mg/kg of patient body weight per day depending on, for example, the patient, and the severity of the thrombotic condition to be treated. The suitable dose for a particular patient can be readily determined. Preferably from 1 to 4 daily doses would be administered typically with from 5 mg to 100 mg of active compound per dose. The concentration of the proteinaceous substance of this invention having Factor $X_a$ inhibition activity required to inhibit Factor $X_a$ when used to inhibit blood coagulation or Factor $X_a$ in a medium such as stored blood can be readily determined by those skilled in the art.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice. Inhibition of Factor $X_a$ is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the proteinaceous substance of this invention having Factor $X_a$ inhibition activity can be added to or contacted with any medium containing or suspected of containing Factor $X_a$ and in which it is desired that blood coagulation be inhibited.

Although the proteinaceous substance of this invention having Factor $X_a$ inhibition activity may survive passage through the gut following oral administration, applicants prefer non-oral administration, for example, subcutaneous, intravenous, intramuscular or intraperitoneal; administration by depot injection; or by implant preparation.

For parenteral administration the proteinaceous substance of this invention having Factor $X_a$ inhibition activity may be administered as injectable dosages of a solution or suspension of the substance in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The proteinaceous substance of this invention having Factor $X_a$ inhibition activity can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The proteinaceous substance of this invention is prepared from leech saliva. Saliva gland extract from either the anterior or posterior salivary glands of *H. ghilianii*, or both, for use in obtaining and purifying the proteinaceous substance of this invention can be obtained in several ways, such as surgical removal of the glands and homogenation, extracting tissue homogenate with, for example, ammonium sulphate solution or other salts, such as sodium chloride or buffers, or with acetone and concentrating or dehydrating the extract, or by ultracentrifugation of the tissue homogenate. The resulting crude salivary gland extract is then subjected to conventional chromatography in order to isolate that portion having $FX_a$ and anticoagulant activity. Applicant has employed chromatography on DEAE-cellulose, an anionic exchange resin and on a heparin-agarose resin eluting with a linear, increasing salt gradient of sodium chloride. Other resins can, of course, be substituted and elution with other salts with various gradients or with organic solvents or mixtures and using varying column flow rates isolating that portion having Factor $X_a$ inhibiting and anticoagulant in the usual manner.

The resulting purified salivary gland extract is then subjected to an affinity chromatography step using Factor $X_a$, such as bovine Factor $X_a$, bound to a chromatography resin, such as those resins typically used in affinity chromatography having chemical groups available for binding Factor $X_a$. Applicant has used Affi-Gel-15, a N-succimidyl ester containing resin available from Bio-Rad Corporation. With this resin, Factor $X_a$ can be bound by incubating the resin together with the Factor $X_a$ with 4-morpholinopropanesulfonic acid and subsequently with ethanolamine. The purified salivary gland extract is chromatographed using this resin eluting with HEPES, 4-(2-hydroxyethyl)-1-piperazineethanesulfonic acid, containing the active site reversible serine protease inhibitor, benzamidine, and collecting that portion having anticoagulant and amidolytic activity. Various conventional variations on this affinity chromatography technique will be readily apparent to those skilled in the art.

The resulting crude proteinaceous substance having Factor $X_a$ inhibiting activity is then further purified. This purification can be accomplished in any conventional manner such as by reverse phase chromatography, a type of chromatography in which the stationary phase is nonpolar and the eluting phase is polar. The stationary phase is typically a hydrocarbon chain chemically bonded to an inert surface, such as glass and the eluting phase is aqueous methanol, acetonitrile or propanol. In the case of hydrophobic interaction chromatography the stationary phase is non-polar and the eluting phase is polar, such as water or aqueous buffer. Applicant has used a C-18 type resin, that is, a resin wherein the hydrocarbon bound to the solid resin is substantially 18 carbon containing hydrocarbon, such as the Aquapore RP-300, C-18 resin eluting with a linear, increasing gradient of aqueous acetonitrile containing trifluoroacetic acid. However, other suitable columns may include $C_3$, $C_4$, $C_6$, $C_8$, etc.

EXAMPLES

This invention is illustrated by the following, nonlimiting examples.

EXAMPLE 1

Preparation of $FX_a$ inhibiting substance from *H. Ghillianii* salivary gland extract and characterization Coagulation, Chromogenic and Fibrin(ogen)olytic Assays. Prothrombin times were determined as one-stage clotting assays and monitored spectrophotometrically with an Electra 800 automatic coagulation timer (Medical Laboratory Automation, Inc.), using the standard programs and reagents recommended by the manufacturer. Briefly, various amounts of either (i) a crude extract of the salivary gland tissue from *Haementeria ghilianii* in 20 mM HEPES, 0.15M NaCl, 2.5 mM $CaCl_2$, pH 7.4 (ii) chromatographic fractions of *H. ghilianii* salivary gland extract in column elution buffer or (iii) purified FXa inhibitor from *H. ghilianii* salivary glands in 20 mM HEPES, 0.15M NaCl, 2.5 mM $CaCl_2$, pH 7.4 were added to 100 μl of citrated normal human plasma. Clot times were determined following the addition of 200 μl of thromboplastin reagent (DADE®) containing 11.6 mM $CaCl_2$. Chromogenic assays of FXa and thrombin amidolytic activities were performed in 96 well microtitre plates (Accurate Chemical and Scientific Corp., Westbury, NY) with methoxycarbonyl-D-cyclohexylglycyl-glycyl-arginine-p-nitroanilide acetate and H-D-hexahydrotyrosyl-L-alanyl-L-arginine-p-nitroanilide acetate, respectively. In these assays, from 0.15 to 16 μg of enzyme in 25 μl of 20 mM HEPES, 0.15M NaCl, pH 7.4 (assay buffer) were added to 25 μl of assay buffer followed by the addition of 50 μl of the appropriate inhibitor sample. The solutions were incubated 10 minutes at room temperature and the assay started by the addition of 100 μl of chromogenic substrates at a final concentration of $2.5\times10^{-4}$M. The amidolytic activities in the absence and presence of inhibitor were monitored spectrophotometrically at 405 nm for p-nitroanilide absorbance with an EL309 Microplate Autoreader (BIO-TEK Instruments) at 1 minute interval recordings.

$^{125}$I-labeled (human) fibrinogen was prepared as described by Knight, et al., *Thromb. Haemostas (Stuttgart)* 46, 593–596 (1981). Fibrinogen (5 mg) in 5 ml of 50 mM Tris-HCl, 0.1M NaCl, 0.025M sodium citrate, pH 7.9 were mixed with 500 μCi of Na$^{125}$I (New England Nuclear, Boston, MA) with 5 μl of 0.045% NaI carrier in a plastic culture tube and chilled on ice. To initiate the reaction, the mixture was transferred to a chilled tube coated with 100 μg of iodogen and stirred gently in an ice bath for 1 hour. To stop the radioiodination reaction, the protein solution was decanted into a plastic culture tube to separate iodogen from the reactants. BSA (5 mg) was then added to the sample and the solution was then fractionated on a 0.5×12 ml column of BioGel P-2 equilibrated in 0.05M Tris-HCl, 0.1M NaCl, pH 7.9 to separate any remaining free $^{125}$I from $^{125}$I-labeled-fibrinogen. The specific radioactivity is $1.9\times10^8$ dpm/mg.

The fibrinogenolytic assay was based on the ability of hementin (S. M. Malinconico, et al., *J. Lab. Clin. Med.* 103, 44–58 (1984)) in chromatographic fractions to degrade $^{125}$I-labeled fibrinogen to trichloroacetic acid soluble $^{125}$I-labeled peptides. In this assay 100 μl of the DEAE-5PW chromatographic fractions were incubated with 50 μg of $^{125}$I-labeled fibrinogen in 227 μl of 50 mM Tris-HCl, 0.1M NaCl, pH 7.9; the sample was adjusted to 10 mM in $CaCl_2$ and then incubated overnight at 37° C. To this was added 100 μl of BSA (3 mg/ml) in incubation buffer followed by the addition of 427 μl of ice cold 20% trichloroacetic acid (TCA). The samples were placed on ice for 2 hours, subjected to centrifugation and the radioactivity in the pellets and supernatants were determined by gamma counting. Fibrinogenolytic activity is expressed as the ratio of the TCA soluble counts to the TCA insoluble counts (TCA sol/TCA ppt).

Preparation of Salivary Gland Extract. Salivary glands of *H. ghilianii*, corresponding to 50 units of hementin (S. M. Malinconico, et al., *J. Lab. Clin. Med.*

103, 44–58 (1984)) activity (49 units/mg protein), were macerated with a glass rod in a 3 ml glass Reacti-Vial (Pierce Chemical Co.) containing 2 ml of 20 mM HEPES, pH 7.8 (extraction buffer). The vial was placed on ice and the contents subjected to microprobe tip sonication (Branson Sonic Power Supply) with four 30 second power bursts using a 30% duty cycle and power level 3. The vial was centrifuged for 5 minutes at 3750 rpm, the supernatant collected and then recentrifuged at 8500 rpm on an Eppendorf tabletop centrifuge. The pellet from the first centrifugation step was resuspended in 2 ml of extraction buffer and the above procedure repeated. The supernatants resulting from the two sonication extractions were then combined and used immediately for purification.

Preparation of Bovine $FX_a$-Affi-Gel-15 Affinity Matrix. Bovine FXa was coupled to Affi-Gel-15 by incubation of 2 mg of purified enzyme in 2 ml of 4-morpholinopropanesulfonic acid (MOPS), pH 7.5 (coupling buffer) with 2.5 ml of resin at 4° C. overnight. The beads were extensively washed and then resuspended in 3 ml of coupling buffer. The beads were next reacted with 0.3 ml of 1M ethanolamine, pH 8.0 overnight at 4° C. and then washed extensively with 0.05M HEPES, 0.1M NaCl, pH 7.5 containing 0.1% Tween-20.

Figure 3:
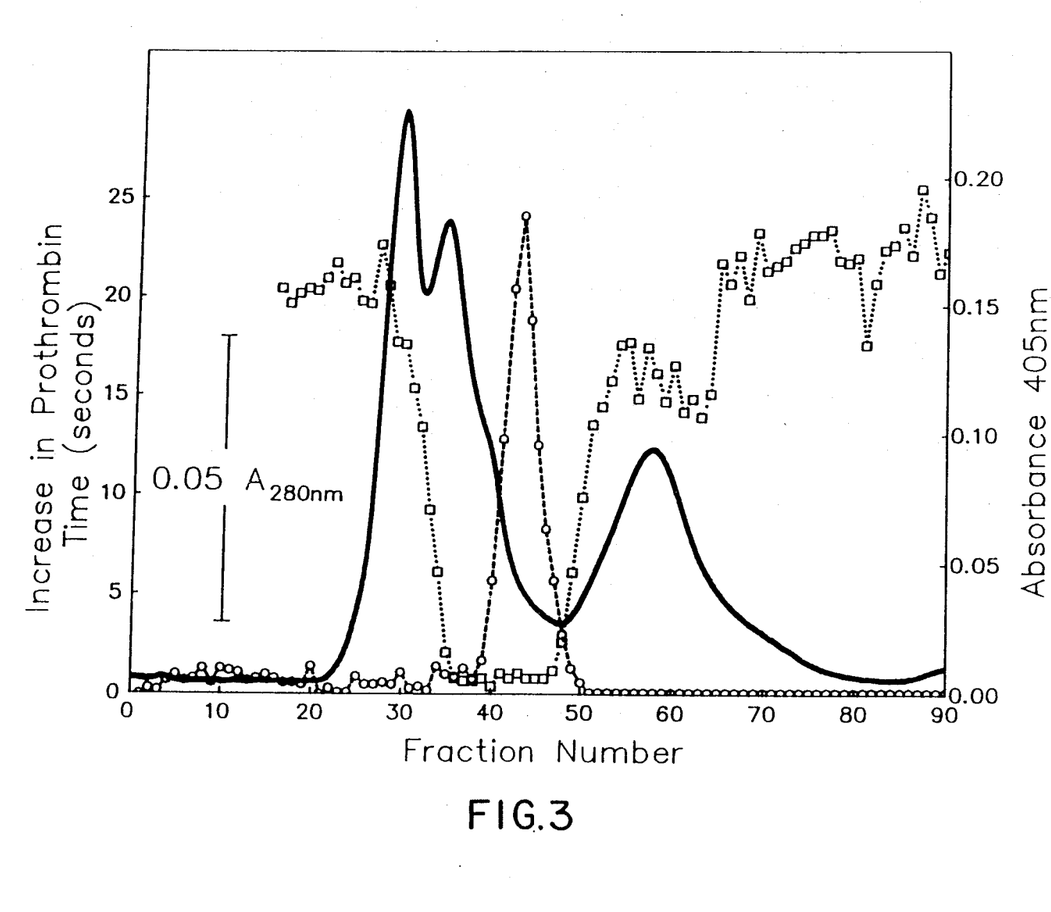
FIG. 3 shows the anticoagulant factions with anti-FXa acitivity of a DEAE column pooled and then fractionated by heparin agarose chromatography.
Figure 4:
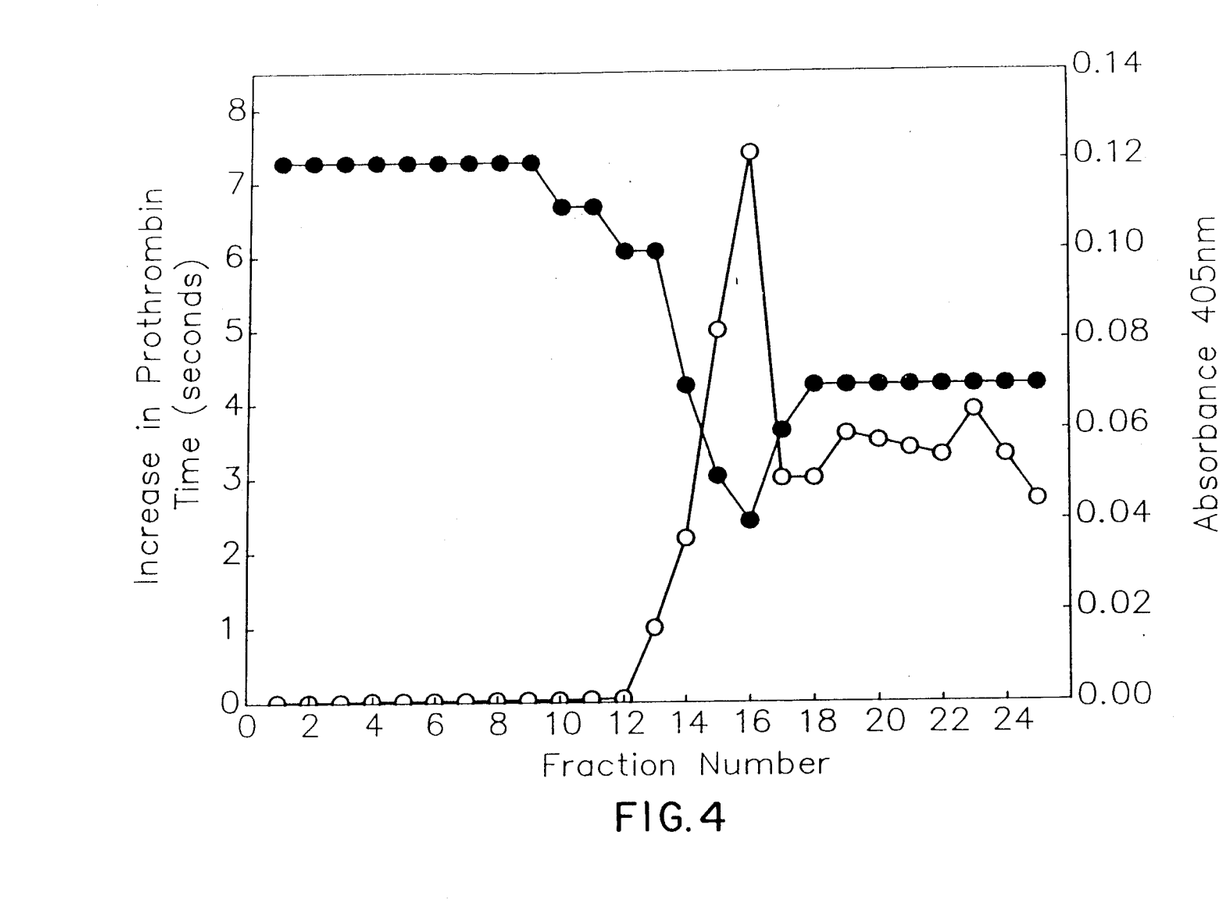
FIG. 4 shows the fractionation of the anticoagulant-/anti-FXa activities by affinity chromatography.

Purification of $FX_a$ Anticoagulant. Salivary gland extract containing 4 mg soluble protein in 4 ml of extraction buffer was applied to a DEAE-5PW (Waters Associates) anion exchange column (0.46×7.5 cm) equilibrated in 20 mM HEPES, pH 7.8 (Buffer A). Proteins were then eluted with a linear gradient of NaCl ranging from 100% Buffer A (initial conditions) to 100% Buffer B (Buffer A containing 0.5M NaCl) over 60 minutes. The flow rate was 1 ml/minute. The fractions eluting between 0.1–0.20M NaCl containing both anticoagulant and anti-$FX_a$ activities were pooled (see FIG. 2), diluted with Buffer A to a conductivity $\leq 10$ mS/cm and then applied to a 0.5×5 cm heparin-agarose column (Bethesda Research Laboratories Life Technologies, Inc.). The further purification of the DEAE fractions with anticoagulant activity on heparin-agarose is shown in FIG. 3. The column was extensively washed with Buffer A and then eluted with a linear salt gradient; the gradient ranged from 100% Buffer A to 100% Buffer B (Buffer A+1M NaCl) over 75 minutes. The flow rate was 1 ml/minute. In some applications, the anti-FXa activity was recovered by fractionating the proteins over a column of bovine $FX_a$-Affi-Gel-15 (FIG. 4). Crude extracts or chromatographic fractions having anticoagulant activity were adjusted to 0.1% Tween-20 and fractionated by affinity chromatography on a column having a 2 ml bed volume of bovine $FX_a$-Affi-Gel-15. The column was extensively washed in 0.05M HEPES, 0.1M NaCl, pH 7.5 containing 0.1% Tween-20 and the proteins eluted with 0.05M HEPES, 0.1% Tween-20, pH 7.5 containing 0.1M benzamidine. Clot and amidolytic assays were performed on 1/500 dilutions of the collected fractions. The column was eluted at a flow rate of 4 ml/hour. Final fractionation of the anticoagulant and amidolytic activities was performed on a 2.1×30 mm Aquapore RP-300, C-18 reverse-phase column with the Applied Biosystems Model 130 protein/peptide separation system. Proteins were eluted with a linear gradient of acetonitrile; the gradient ranged from 100% Buffer A (0.1% trifluoroacetic acid in $H_2O$) to 100% Buffer B (0.07% trifluoroacetic acid/70% acetonitrile/29.93% $H_2O$) over 40 minutes. Fractions (see FIG. 5) containing protein were dried overnight on a Savant speed vac system. Samples were redissolved in 0.1% trifluoroacetic acid/$H_2O$ and various aliquots analyzed by SDS polyacrylamide gel electrophoresis gas-phase microsequencing, amino acid analysis and for anticoagulant and amidolytic activities.

Analytical Polyacrylamide Gel Electrophoresis. Polyacrylamide gels (8×8 cm and 1 mm thick), 20% and 12% in acrylamide, containing a 3% stacking gel were placed in a Mighty Small electrophoresis unit (Hoefer Scientific Co.) and subjected to a constant current of 10 mA/gel. Gels contained 0.25M Tris-HCl, pH 9.0 and 0.1% sodium dodecyl sulfate (SDS). Electrophoresis was performed in 25 mM Tris-HCl, 0.2M glycine, 0.1% SDS, pH 8.4. Dried samples were solubilized in 35 $\mu$l of 10 mM Tris-HCl, pH 6.8, 1% SDS, 20% sucrose, 1 mM EDTA, 6M urea, 1% 2-mercaptoethanol and 0.03% bromophenol blue; prior to electrophoresis, samples were heated at 60° C. for 15 minutes. Gels were fixed and the proteins detected by the silver stain procedure of Merrill, et al, Anal. Biochem., 105, 361 (1980). Apparent molecular weights of proteins were determined by extrapolation from a standard point of the logarithm of the molecular weights versus the electrophoretic mobility of standard proteins. The protein standards were phosphorylase B (94,000), bovine serum albumin (67,000) ovalbumin (43,000), carbonic anhydrase (30,000), $\alpha$-chymotrypsinogen (25,700), soybean trypsin inhibitor (20,000), $\beta$-lactoglobulin (18,400), $\alpha$-lactalbumin (14,400), lysozyme (14,300) bovine trypsin inhibitor (6,200) and insulin (3,000).

Sequence Analysis. Automated Edman degradations were performed on a Model 470A protein-peptide sequencer (Applied Biosystems, Inc.) with reagents, instructions and standard programs supplied by the manufacturer. The phenylthiohydantoin-derivitized amino acids were analyzed at each cycle on a Model 120 PTH-Analyser (Applied Biosystems, Inc.) directly on-line with the 470A gas-phase sequencer.

Amino Acid Analysis. Autosampler microvials (Hewlett Packard), used as hydrolysis tubes, were sonicated in methanol then heated in a furnace at 500° C. for 4 hours. Peptides were hydrolyzed by gas phase hydrolysis in a Picotag Workstation (Waters Associates) at 105° C. for 20 hours with 200 $\mu$l of constant boiling HCl (Pierce Chemical Co.) containing a few microliters of liquified phenol (MCB). Hydrolyzed samples were taken to dryness in a speed vac concentrator (Savant), dissolved in a small volume (typically 15–30 $\mu$l) of 0.1N HCl and placed in the autosampler of a Model 1090 HPLC (Hewlett Packard). Amino acid analysis was performed using the Aminoquant analyzer by Hewlett Packard in the high sensitivity configuration (fluorescence detection). Amino acids were determined after precolumn derivatization with first O-phthaladehyde (OPA) for primary amino acids and then 9-fluorenylmethyl chloroformate (FMOC) for secondary amino acids. The derivatized amino acids were separated by reverse-phase HPLC with columns, reagents and instructions supplied by the manufacturer. This system accurately quantitates 1–500 pmoles of aminoacyl mass.

Figure 1:
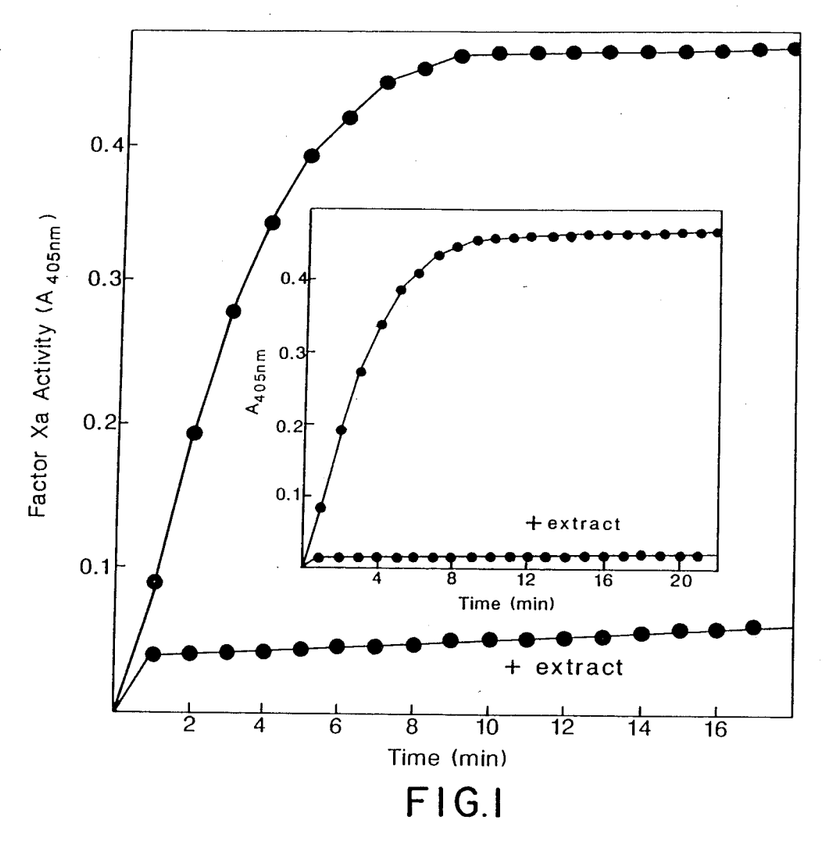
FIG. 1 shows the anti-FXa activity in crude salivary gland extracts of *H. ghilianii*.

FIG. 1 shows the anti-$FX_a$ activity in crude salivary gland extracts of H. ghilianii. The active principle inhibits both human (see inset) and bovine $FX_a$ but not human and bovine thrombins (data now shown).

Figure 2A:
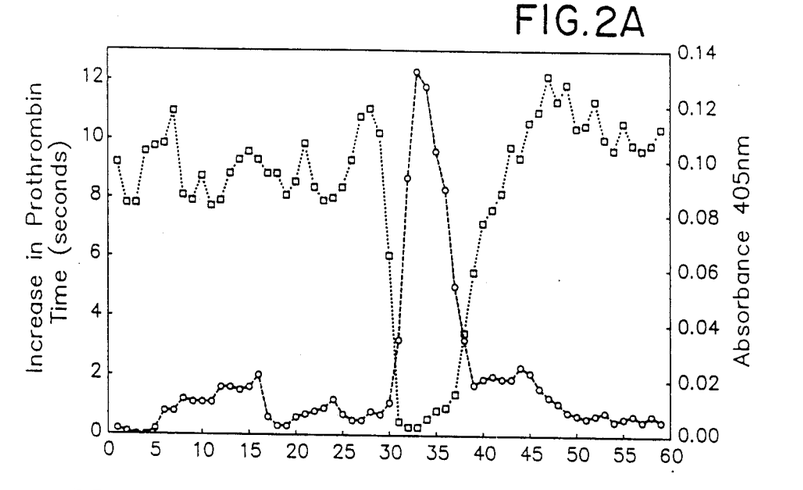
FIGS. 2A and B show the chromatography of 4 mg of the soluble protein extract by anion exchange on DEAE.
Figure 2B:
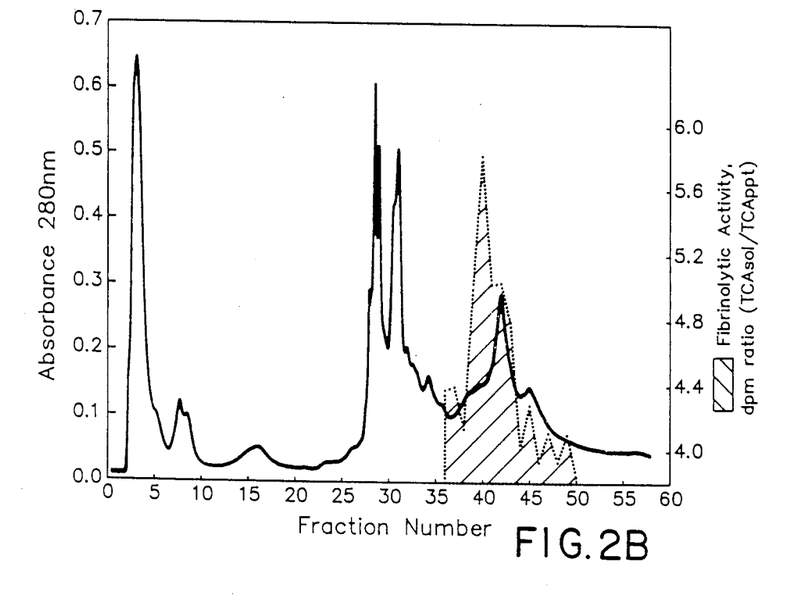

FIG. 2 shows the chromatography of 4 mg of the soluble protein extract by anion exchange on DEAE. The anticoagulant and FXa inhibitory activities coelute between 0.1–0.16M NaCl (panel A) between fractions 30–35. The fibrinogenolytic activity, without anti-FXa activity, eluted above 0.20M NaCl (panel B) between fractions 37–44 (hatched area). This material promoted clot (fibrin) lysis, degraded $^{125}$I-labeled fibrinogen (FIG. 2, Panel B) and was shown to degrade the $\alpha$, $\beta$, and $\gamma$ chains of purified fibrinogen by SDS-PAGE (not shown). The fibrin(ogen)olytic action of this fraction is attributable to hementin. Moreover, fractions with anti-FXa activity showed no fibrin(ogen)olytic activity. Based on the results of FIGS. 1 and 2, the inhibitor eluting between 0.1–0.16M NaCl is not due to hirudin of Hirudo medicinalis (J. Dodt, et al., Biol Chem. Hoppe-Seyler 366, 379–385 (1985)) or hementin, the fibrin(ogen)olytic component of Haementeria ghilianii (S. M. Malinconico, et al., J. Lab. Clin. Med. 103, 44–58 (1984)). As is shown in FIG. 2, 25 $\mu$l of the fractions having peak activity prolonged the prothrombin time by 16 seconds and completely inhibited 17 ng of $FX_a$ in the amidolytic assay. Based on the assays of the DEAE fractionated extract, the $FX_a$ inhibiting activity accounts for the major anticoagulant activity.

The anticoagulant fractions with anti-$FX_a$ activity from the DEAE column were pooled and then fractionated by heparin agarose chromatography (FIG. 3). Anticoagulant and anti-FXa amidolytic activities co-eluted between 0.45–0.55M NaCl. Moreover, 25 $\mu$l of fractions showing peak anticoagulant activity prolonged the prothrombin time by $\simeq$17 seconds and completely inhibited the hydrolysis of the chromogenic substrate by 16 ng of purified $FX_a$.

Fractionation of the anticoagulant/anti-$FX_a$ activities by affinity chromatography on $FX_a$-Affi-Gel-15 is shown in FIG. 4. As is shown, the anticoagulant and anti-$FX_a$ activities were eluted together from the column with 0.1M benzamidine, a reversible active site serine protease inhibitor.

Figure 5:
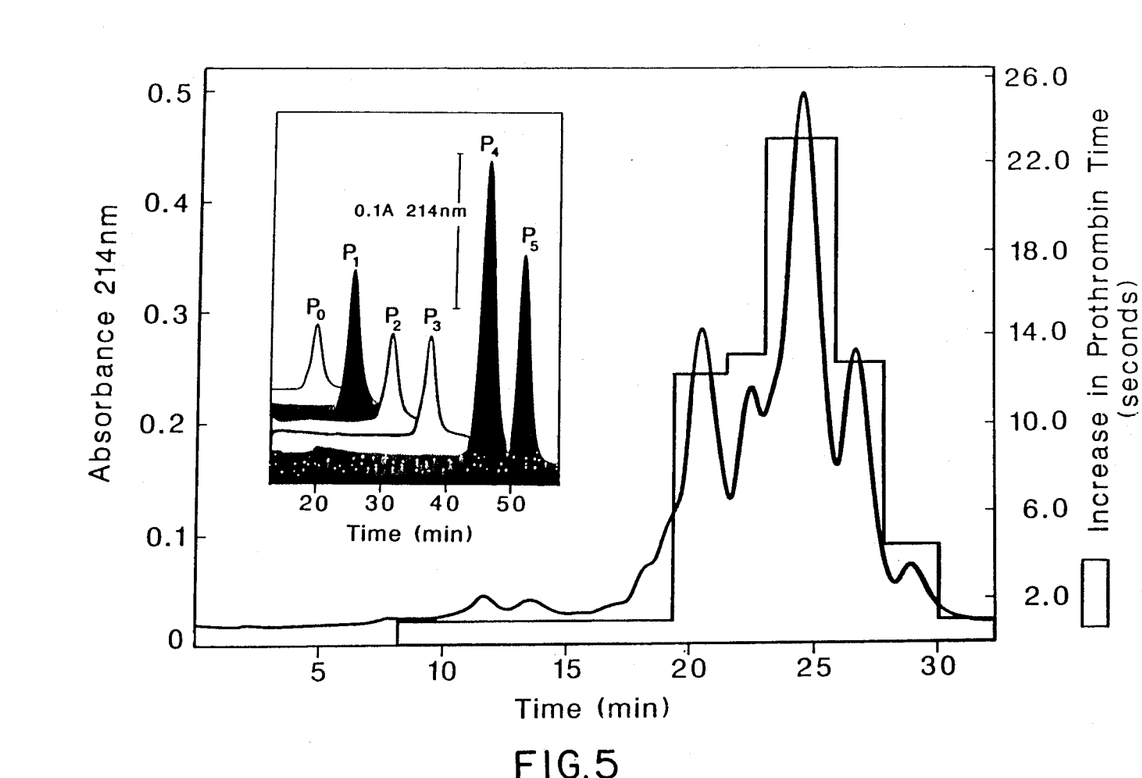
FIG. 5 shows further fractionation of the inhibitor by microbore reverse-phase HPLC.

Further fractionation of the inhibitor by microbore reverse-phase HPLC is shown in FIG. 5. As can be seen, four minor and two major peaks were resolved with the anticoagulant activity distributed across the multiplet of peaks. Refractionation yielded six discrete peaks, designated $P_0$–$P_5$ (see inset). Of these, $P_4$ and $P_5$ showed the major anticoagulant and anti-FXa activities with $P_1$–$P_3$ showing moderately less activity. No activity was detected in $P_0$.

Figure 6:
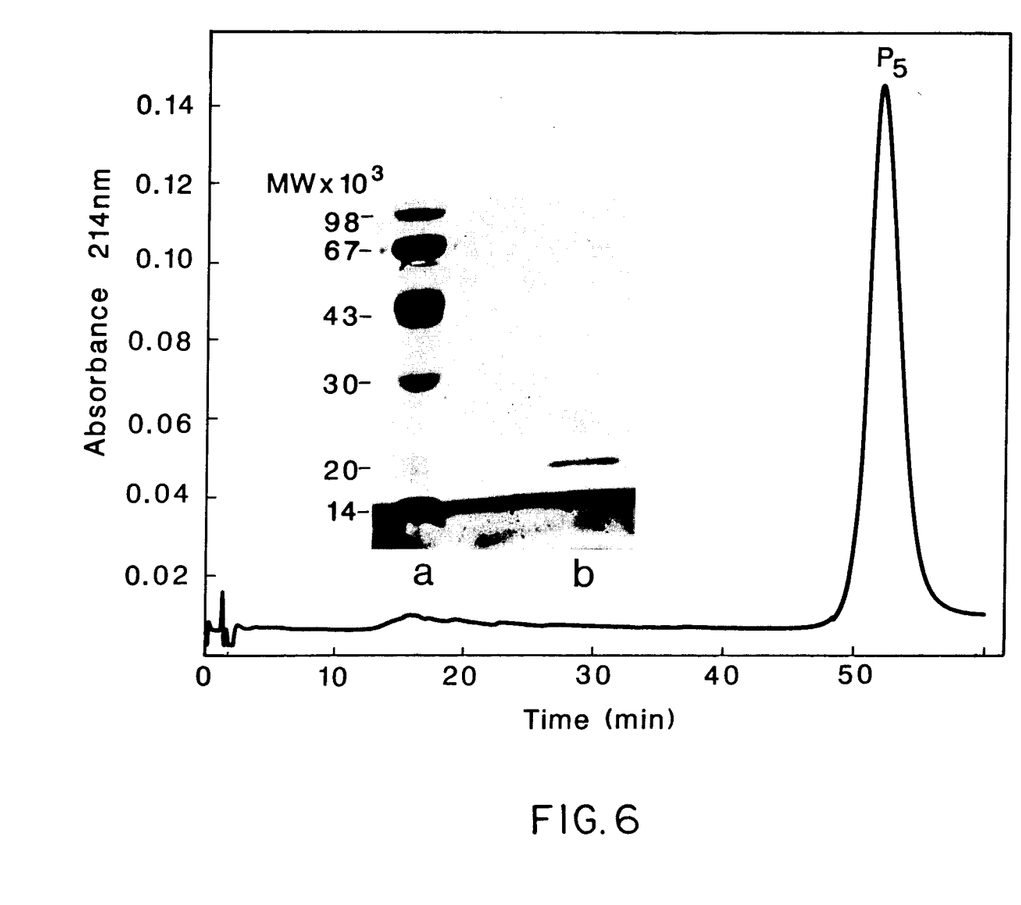
FIG. 6 shows the chromatographic profile of $P_5$ on microbore reverse-phase HPLC.

SDS PAGE (20% acrylamide) of fractions $P_0$–$P_5$ verified that these proteins have similar mobilities with apparent molecular weights $\simeq$18,000 (not shown). FIG. 6 shows the chromatographic profile of $P_5$ on microbore reverse-phase HPLC. The inset shows a 12% SDS-PAGE (12% acrylamide) of $P_5$. This pure component has an apparent molecular weight of 18,000, i.e., the apparent molecular weight of the purified $FX_a$ inhibitor does not vary significantly with polyacrylamide gel concentration between 12% and 20% suggesting it is not highly glycosylated.

Figure 7:
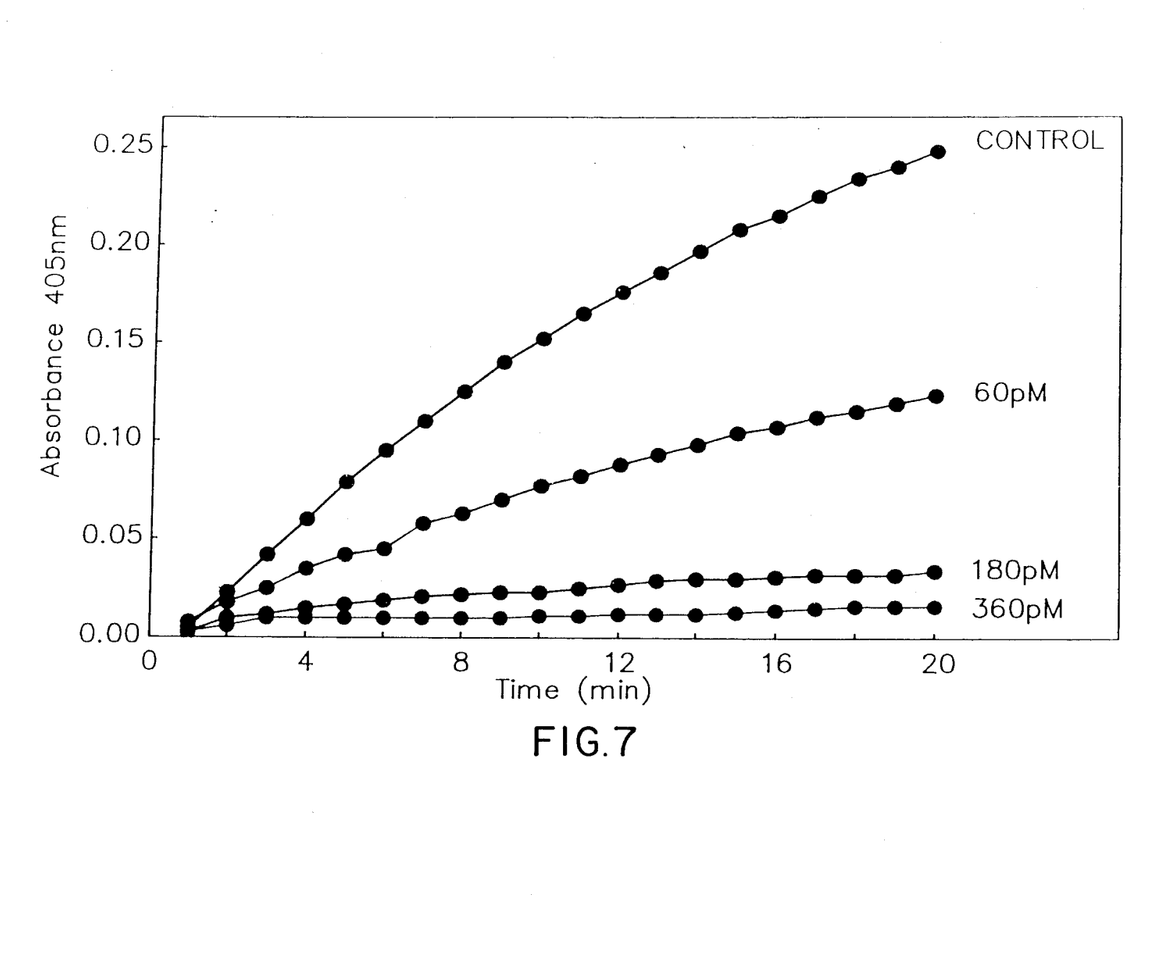
FIG. 7 shows the dose-dependent inhibition of FXa by $P_5$.

FIG. 7 shows the dose-dependent inhibition of $FX_a$ by $P_5$. The concentration of $P_5$ giving half-maximal inhibition is 60 picomolar.

Table I shows the amino acid compositions of fractions $P_0$–$P_5$. The amino acid contents of $P_1$–$P_5$ were highly similar with respect to most residues with the exceptions that $P_4$ and $P_5$ showed slightly higher Asx and Glx and significantly higher Lys and Pro. $P_0$ differed significantly from $P_1$–$P_5$ in its content of Asx, Glx, Thr, Arg, Val, Met, Ile, Lys and Pro. The decreased activity of $P_1$, $P_2$, and $P_3$ is possibly associated with the significantly decreased content of Lys and Pro. The overall similarity in composition, with the exception of Lys and Pro, suggests that $P_1$–$P_5$ are sequence related proteins.

EXPLANATION OF FIGURES

FIG. 1. Inhibition of $FX_a$ by crude salivary gland extract of Haementeria ghilianii. Approximately 11 $\mu$g of salivary gland extract (soluble protein) were added to 16 ng of purified $FX_a$. The sample was incubated for 10 minutes at room temperature and the amidolytic activity determined after the addition of methoxycarbonyl-D-cyclohexylglycyl-glycyl-arginine-p-nitroanilide acetate; p-nitroanilide formation was monitored spectrophotometrically at 1 minute interval recordings at 405 $\eta$m. Top curve: bovine $FX_a$ and chromogenic substrate; bottom curve: bovine $FX_a$, salivary gland extract and chromogenic substrate. Inset: (top curve) human $FX_a$ and chromogenic substrate: (bottom curve) human $FX_a$, salivary gland extract and chromogenic substrate. Salivary gland extract of H. ghilianii did not inhibit the hydrolysis of H-D-hexahydrotyrosyl-L-alanyl-L-arginine-p-nitroanilide acetate by bovine and human thrombins (not shown).

FIG. 2. Fractionation of crude salivary gland extract (4 mg soluble protein) on a 0.46×7.6 cm DEAE anion exchange column. Proteins were eluted with a linear gradient of NaCl in 20 mM HEPES, pH 7.8 (see methods for details). The flow rate was 1 ml/minute and 1 ml fractions were collected. Panel A: Anticoagulant activity (open circles) was determined by a one-stage clot assay as the prolongation in prothrombin time. Inhibition of $FX_a$ was measured at 405 nm for inhibition of p-nitroanilide formation (open squares) using the chromogenic substrate methoxycarbonyl-D-cyclohexylglycyl-glycyl-arginine-p-nitroanilide acetate. Panel B: This panel shows the H. ghilianii protein elution profile monitored by absorption at 280 nm. The fibrinogenolytic activity is shown by the cross-hatched area. This activity does not coelute with the anti-$FX_a$ or major anticoagulant activities.

FIG. 3. Fractionation of the partially purified $FX_a$ inhibitor by heparin agarose chromatography. The DEAE fractions with coeluting anticoagulant and anti-$FX_a$ activities were pooled and loaded onto a 0.5×5 cm column of heparin agarose. Proteins were eluted with a linear gradient of NaCl to 1M in 20 mM HEPES, pH 7.8. The flow rate was 1 ml/minute and 1 ml fractions were collected. Anticoagulant activity (open circle) was determined by a one-stage clot assay as the prolongation in prothrombin time. Inhibition of $FX_a$ was measured at 405 nm for inhibition of p-nitroanilide formation (open square) using the chromogenic substrate methoxy-D-cyclohexylglycyl-glycyl-arginine-p-nitroanilide acetate.

FIG. 4. Fractionation of the $FX_a$ inhibitor by affinity chromatography on bovine $FX_a$-Affi-Gel-15. Proteins were eluted from the column with 0.1M benzamidine. Flow rate was 4 ml/hour and 1.2 ml fractions were collected; 1/500 dilutions of the chromatographic fractions were assayed for anticoagulant (open circle) and anti-$FX_a$ (filled circle) activities as described.

FIG. 5. Purification of the H. ghilianii anti-$FX_a$ principle(s) by reverse-phase HPLC. Peak fractions with coeluting anticoagulant and anti-$FX_a$ activities were fractionated by microbore reverse-phase HPLC on a 2.1×30 mm Aquapore RP-300 column. The shaded area shows the anticoagulant acitvity distributed across the peak fractions. The inset shows the rechromatography of the initial reverse-phase separation on the same column. By rechromatography discrete, non-overlapping peaks were obtained. The major $FX_a$ inhibitory activity was found in $P_4$ and $P_5$ (heavy shading); activity was also detected in $P_1$, $P_2$ and $P_3$ (lighter shading). No activity was detected in $P_0$ (no shading).

FIG. 6. Microbore reverse-phase HPLC of $P_5$. Absorbance was monitored at 214 nm for the *H. ghilianni* protein $P_5$. The inset shows a SDS PAGE (12% acrylamide) of $P_5$ isolated by microbore reverse-phase HPLC. Lane a shows the molecular weight standard proteins and lane b, purified $P_5$. Proteins were detected by silver stain according to the method of Merrill, et al.

FIG. 7. The dose-dependent inhibition of $FX_a$ (0.15 ng) by purified $P_5$ was tested at the indicated concentrations for its ability to inhibit the hydrolysis of methoxycarbonyl-D-cyclohexylglycyl-glycyl-arginine-p-nitroanilide acetate. p-Nitroanilide formation was monitored at 405 nm.

TABLE I

Amino Acid Analyses[a] of Fractions $P_0$–$P_5$ Obtained from Salivary Gland Extracts of *Haementeria Ghilianii* by Microbore Reverse-Phase HPLC

| Amino Acid | $P_5$ | $P_4$ | $P_3$ | $P_2$ | $P_1$ | $P_0$ |
|---|---|---|---|---|---|---|
| Asx | 17 | 18 | 14 | 16 | 17 | 11 |
| Glx | 22 | 24 | 19 | 19 | 20 | 14 |
| Ser | 9 | 10 | 7 | 8 | 8 | 7 |
| His | 2 | 2 | 2 | 2 | 2 | 2 |
| Gly | 14 | 18 | 13 | 13 | 14 | 10 |
| Thr | 9 | 10 | 10 | 10 | 11 | 7 |
| Ala | 6 | 6 | 6 | 6 | 6 | 6 |
| Arg | 18 | 20 | 18 | 19 | 21 | 13 |
| Tyr | 6 | 6 | 6 | 6 | 6 | 5 |
| Val | 7 | 7 | 5 | 7 | 7 | 4 |
| Met | 5 | 5 | 5 | 5 | 5 | 3 |
| Ile | 8 | 8 | 7 | 7 | 8 | 5 |
| Phe | 4 | 4 | 3 | 4 | 4 | 3 |
| Leu | 9 | 9 | 10 | 11 | 1 | 9 |
| Lys | 12 | 14 | 7 | 5 | 6 | 4 |
| Pro | 17 | 16 | 6 | 6 | 6 | 3 |

[a]Expressed as residues per mole of protein. Values were normalized to an Ala content of 6 residues/mole.

I claim:

1. A process for isolating a proteinaceous substance having Factor $X_a$ inhibiting activity from the saliva of the leech *Haementeria ghilianii* which comprises
   (a) subjecting the saliva to an increasing salt gradient on an anionic ion exchange resin and segregating that portion of the eluant having Factor $X_a$ inhibiting activity;
   (b) subjecting the isolated fractions from part (a) to affinity chromatography based on heparin, Factor $X_a$, or both heparin and Factor $X_a$ and segregating that portion having anticoagulant and amidolytic activity; and
   (c) subjecting the isolate from part (b) to reverse phase high pressure liquid chromatography and segregating that portion of the eluant having Factor $X_a$ inhibiting activity.

2. A process of claim 1 wherein the anionic exchange resin is DEAE-cellulose.

3. A process of claim 1 wherein the HPLC resin is an N-succimidyl ester containing resin.

* * * * *